US008600096B2

(12) United States Patent
Lin

(10) Patent No.: US 8,600,096 B2
(45) Date of Patent: Dec. 3, 2013

(54) SURFACE TREATMENT FOR EAR TIPS

(75) Inventor: Lifun Lin, Lincoln, MA (US)

(73) Assignee: Bose Corporation, Framingham, MA (US)

( * ) Notice: Subject to any disclaimer, the term of this patent is extended or adjusted under 35 U.S.C. 154(b) by 126 days.

(21) Appl. No.: 13/196,526

(22) Filed: Aug. 2, 2011

(65) Prior Publication Data

US 2013/0034258 A1 Feb. 7, 2013

(51) Int. Cl.
*H04R 25/00* (2006.01)
(52) U.S. Cl.
USPC .......... 381/380; 381/374; 381/370; 381/150; 381/328; 427/2.1
(58) Field of Classification Search
USPC .......... 381/328, 370–372, 380; 181/129–130, 181/135; 128/864
See application file for complete search history.

(56) References Cited

U.S. PATENT DOCUMENTS

| | | | |
|---|---|---|---|
| 5,449,865 A * | 9/1995 | Desnick et al. | 181/131 |
| 6,022,311 A | 2/2000 | Juneau et al. | |
| 7,600,604 B2 * | 10/2009 | Babcock et al. | 181/130 |
| 7,886,745 B2 * | 2/2011 | Purcell et al. | 128/864 |
| 8,121,325 B2 * | 2/2012 | Atamaniuk et al. | 381/322 |
| 8,280,093 B2 * | 10/2012 | Siahaan et al. | 381/380 |
| 2010/0098281 A1 * | 4/2010 | Urso et al. | 381/328 |
| 2011/0051979 A1 * | 3/2011 | Lee et al. | 381/380 |
| 2011/0091061 A1 * | 4/2011 | von Dombrowski et al. | 381/330 |

FOREIGN PATENT DOCUMENTS

| | | |
|---|---|---|
| WO | 2006/084172 A1 | 8/2006 |
| WO | 2007/044766 A1 | 4/2007 |

OTHER PUBLICATIONS

Why Use Parylene Coatings?, Parylene Engineering, 2010.*
NuSil Technology Releases Low Coefficient of Friction Silicone Coating for Healthcare Applications, SpecialChem, 2010.*
Types and Properties of Moldable Silicone Rubber, Albright Technologies Inc. 2011.*
Coefficients of Friction for Teflon, 2004.*
Acheson, Emralon 8301 Product Data Sheet, Retrieved from the Internet on May 23, 2013: http://henkelcorp.com/industrial/product-search-1554.htm?nodeid=8798045667329.*
International Search Report and the Written Opinion of the International Searching Authority dated Nov. 6, 2012 for PCT/US2012/049098.

* cited by examiner

*Primary Examiner* — Brian Ensey
*Assistant Examiner* — Sabrina Diaz

(57) ABSTRACT

An ear tip includes a body shaped to fit at least partially into the outer ear of a wearer and having a coefficient of friction greater than 2.0. The body has an outer surface having a permanent coating on at least the part shaped to fit into the outer ear with a coefficient of friction of less than 2.0.

28 Claims, 5 Drawing Sheets

400

500

SURFACE TREATMENT FOR EAR TIPS

BACKGROUND

This disclosure relates to a surface treatment for ear tips including noise-blocking earplugs and ear interfaces for audio headphones or hearing aids.

Earplugs for blocking sound are available in a variety of materials and shapes, and are generally designed to fit inside some part of the ear canal and/or outer ear. Many types of audio headphones and most hearing aids also include parts called "ear interfaces" designed to fit inside some part of the ear canal and/or outer ear. Ear interfaces may serve to hold the device in place, to control acoustic coupling between acoustic elements and the wearer's ear drum, and to block outside sound from entering the ear. Headphone ear interfaces may be custom-molded to a particular wearer's ear or may have a universal fit designed to fit some portion of the general population. Hearing aid ear interfaces are almost always custom-molded. Noise-blocking earplugs may also be custom molded, especially for workers who spend significant time in high-noise environments, such as factory workers or soldiers. We use ear tips generically to refer to both noise-blocking earplugs and audio headphone or hearing aid ear interfaces.

As shown in FIG. 1, an earplug 30 maintains contact with the skin of the ear 10 in order to remain in place and to block sound from passing through any gaps between the earplug and the skin. In particular, earplugs designed to block sound need to have intimate contact with the ear skin, which is commonly achieved through the use of soft materials such as silicone that conform to the shape of the ear.

FIG. 1 also identifies several parts of human ear anatomy referred to below. The ear canal 12 is the passageway from the eardrum 14 through the head 16 to the outer environment. The pinna 18 refers to the structures of the ear located outside of the head. The pinna includes several structures, including the helix 20, antihelix 22, tragus 24, and antitragus 26. In the figure of FIG. 1, the tragus 24 and part of the helix 20 would be forward of the plane where the section of the head 16 was taken, as shown by the dotted lines. The concha 28 is the bowl-shaped space around the outer end of the ear canal, and is bounded by the tragus, antitragus, and antihelix.

SUMMARY

In general, in one aspect, an ear tip includes a body shaped to fit at least partially into the outer ear of a wearer and made of a material having a coefficient of friction of greater than 2.0. The body has an outer surface having a permanent coating on at least the part shaped to fit into the outer ear with a coefficient of friction of less than 2.0.

Implementations may include one or more of the following. The body may include silicone. The material composing the body may have a coefficient of friction of greater than 3.0. The coating may include a distinct layer of material having different material properties than the body. The layer of material may include silicone having a coefficient of friction in the range of 0.2 to 1. The layer may be composed of a plurality of nodules of the material. The nodules may each have a diameter between around 25 to 100 µm and a height of around 10 µm, and may be spaced around 100 µm apart. The coating may include a layer of NuSil MED 6670 silicone. The coating may include a layer of silicone selected from the group consisting of Dow 1-2620, Dow 1-2557, and Dow 3715. The coating may include Parylene. The layer of material may have a hardness greater than that of the body. The layer of material may be uniformly distributed over the body. The body may have a hardness of 20 A durometer or less. The body may have a hardness of OO40 durometer. The coating may have a coefficient of friction of 1.0 or less. The coating may have a coefficient of friction of 0.2. The ear tip may be shaped to serve as an ear interface for an audio reproduction device. The ear tip may include a cushion section shaped to fit the lower concha of the wearer's ear and having an engagement section for coupling to the audio reproduction device, a nozzle shaped to fit at least partially into the ear canal of the wearer's ear, and a passage through the ear tip to allow sound generated by the audio reproduction device to pass through the nozzle and into the ear canal. The ear tip may include a retention feature extending from the cushion section and shaped to fit along the antihelix of the wearer's ear. The coating may cover the outer surface over only a portion of the total surface area of the ear tip.

In general, in some aspects, fabricating an ear tip includes filling mold cavity with a material having a coefficient of friction, when cured, of greater than 2.0 to form a body of the ear tip, removing the body from the mold, and coating the body with a material having a coefficient of friction, when cured, of less than 2.0.

Implementations may include one or more of the following. Coating the body may include spraying NuSil MED 6670 silicone onto the body. Coating the body may include dipping the body into a silicone selected from the group consisting of Dow I-2620, Dow 1-2557, and Dow 3715. Coating the body may include applying Parylene to the body using vapor deposition.

In general, in one aspect, a set of headphones for audio reproduction includes pair of earphones, each earphone including an electroacoustic transducer inside a housing, and a pair of ear interfaces formed at least in part of silicone having a coefficient of friction of greater than 2.0. The ear interfaces each include a cushion section shaped to fit the lower concha of the wearer's ear and having an engagement section for coupling to one of the earphones, a nozzle shaped to fit at least partially into the ear canal of the wearer's ear, a passage through the ear interface, to allow sound generated by the earphone to pass through the nozzle and into the ear canal, and an outer surface having a permanent coating with a coefficient of friction of less than 2.0.

The set of headphones may additionally include a second pair of ear interfaces formed of the same materials and including the same features of the first pair, but with a different sized cushion.

In general, in one aspect, an ear tip includes a body shaped to fit at least partially into the outer ear of a wearer and formed of a first material having a first coefficient of friction. The body has an outer surface at least partially formed of a second material on at least the part shaped to fit into the outer ear, the second material having a second coefficient of friction. The second coefficient of friction is less than the first coefficient of friction.

Advantages include reducing the tackiness of soft materials (e.g., soft silicone) while providing a very low friction surface in an ear tip. This allows easier, more consistent, and safer insertion of the ear tip, better acoustic sealing, and improved comfort during extended use.

Other features and advantages will be apparent from the description and the claims.

DESCRIPTION

Ear tips are commonly made of soft materials such as silicone. Unfortunately, such soft materials tend to have a high coefficient of friction, which causes it to grab the skin and prevent the ear tip from deforming smoothly and conforming to the ear contour as it is inserted. This grabbing also causes the act of inserting a silicone ear tip to be uncomfortable to the wearer and may cause discomfort with extended wear of the ear tip. In addition, soft materials are often tacky and attracts dirt, which can compromise its acoustic seal and damage the tissues of the wearer's ear. A surface treatment as described below improves the comfort of silicone ear tips and the quality of their fit. This surface treatment reduces the tackiness of the soft material of the ear tip, and also provides a low friction surface. The low friction surface enables the ear tips to be smoothly inserted into the ear, achieving a better seal without discomfort from pinching.

Figure 2A:
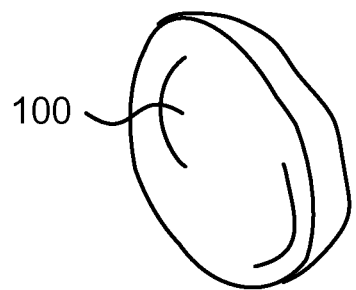
FIG. 2A shows a noise-blocking earplug.
Figure 2B:
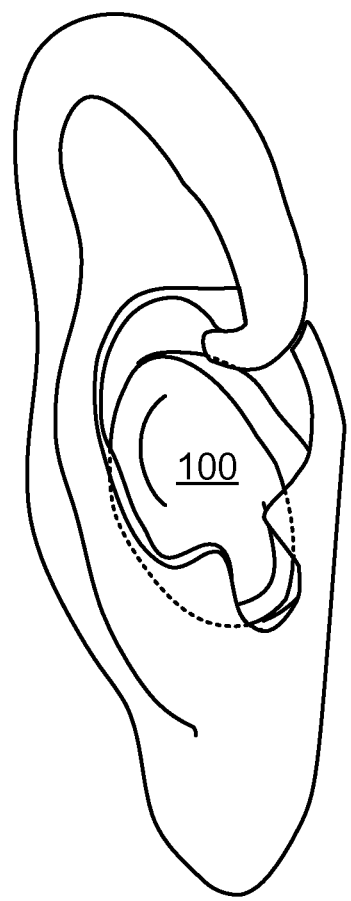
FIG. 2B shows the noise-blocking earplug of FIG. 2A in an ear.
Figure 3A:
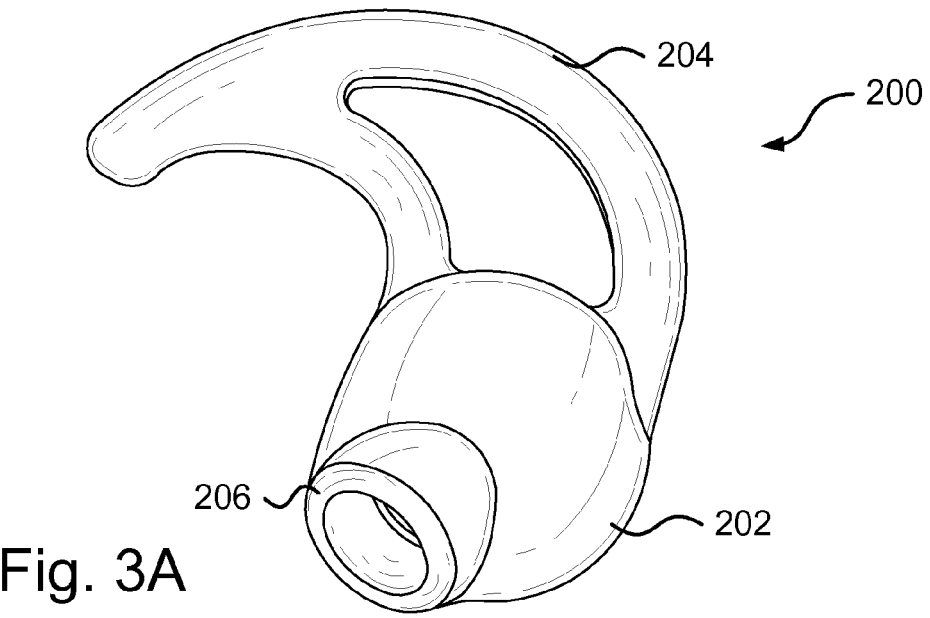
FIG. 3A shows an audio headphone ear interface.
Figure 3B:
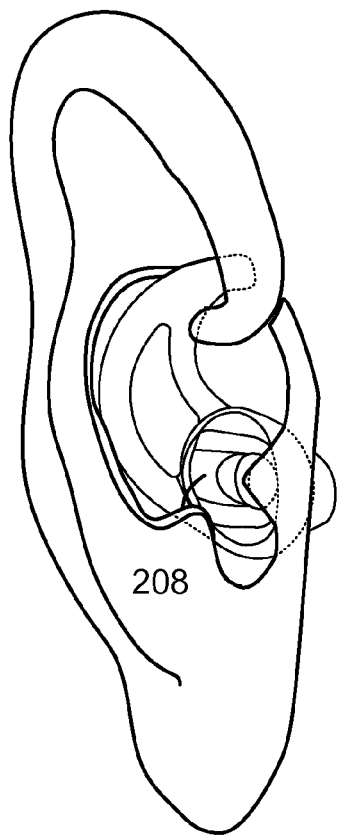
FIG. 3B shows the audio headphone ear interface of FIG. 3A in an ear.

FIGS. 2A and 3A show an example noise-blocking earplug 100 and headphone ear interface 200, respectively. FIGS. 2B and 3B show the corresponding earplug 100 and ear interface 200 in an ear. The example headphone ear interface shown in FIG. 3A is based on the ear interfaces used by Bose Corporation of Framingham, Mass. for its in-ear audio headphones and communications headsets.

The earplug 100 in FIG. 2 is a single bulbous plug of material that fits in the lower part of the concha, behind the tragus and antitragus and abutting the end of the helix. In this position, the earplug blocks but does not enter the ear canal. In some examples, the earplug 100 could have an additional extension that protrudes into the ear canal, like the extension 206 shown in FIG. 3A.

Figure 1:
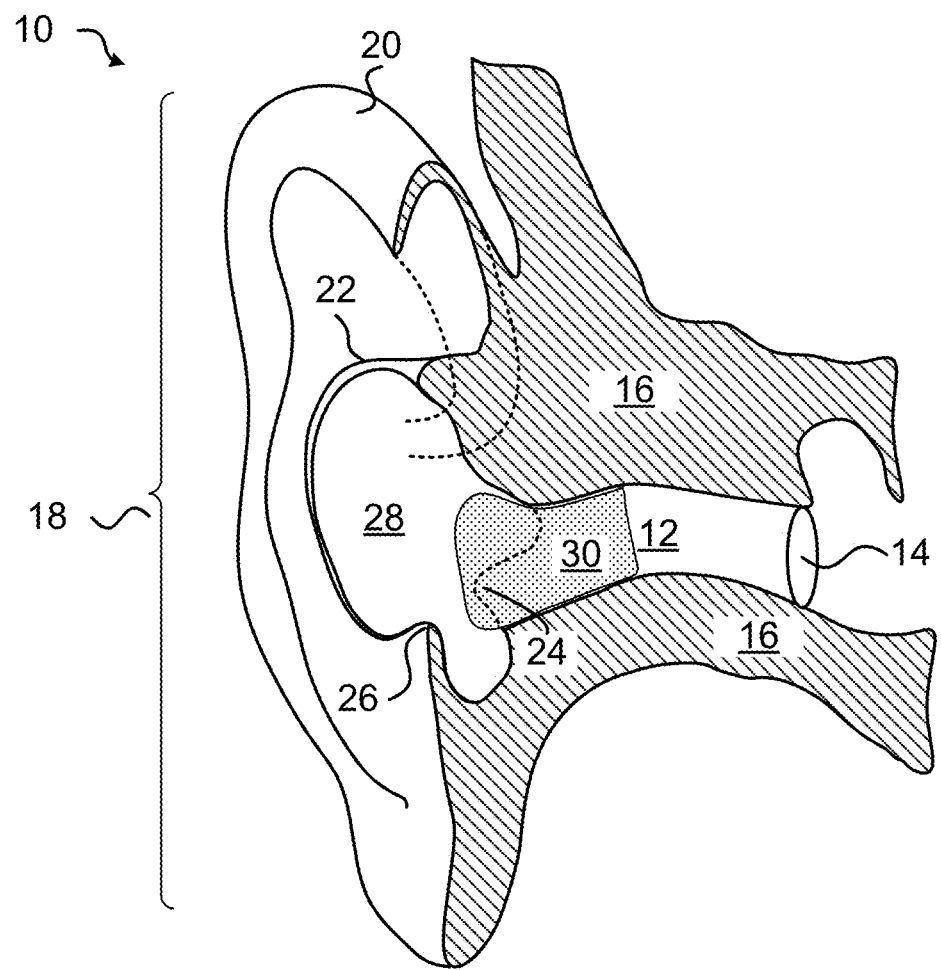
FIG. 1 shows a cross-section of a human ear with an earplug inserted.

In the example of FIG. 3A, the ear interface 200 includes a lower body 202 designed to sit in the concha of the wearer's ear. FIG. 3A shows the side of the ear interface 200 that is pressed into the ear; the opposite side is visible in FIG. 3B. An extension 204 rests under the antihelix and acts as a retention feature to help further secure the ear interface in the ear. Other ear tip designs, such as the simple plug shown in FIG. 1 and similar ear interfaces for headphones, use only pressure against the ear canal (and resulting friction between the ear tip and skin) to hold themselves in place. Custom-molded ear tips may fill the entire concha and the outer end of the ear canal with material in order to better block sound and achieve a more secure fit.

Referring again for FIG. 3A, the headphone ear interface 200 also includes an extension 206 that extends a short distance into the ear canal to improve the acoustic seal and to better control the acoustic coupling of the headphone (not shown) to the ear drum. A headphone interface 208 couples the ear interface to an audio headphone (not shown). The ear interface may be removable or may be permanently attached to the headphone. In some examples, the ear tips 100 or 200 include an inner core of a harder silicone than the outer core. This can serve to strengthen the ear tip, to maintain its overall shape, and to provide a more secure attachment point for headphones, while keeping the resiliency of the outer layer of softer silicone. For reference, see the dual-hardness ear interfaces described in U.S. Pat. No. 7,916,888, incorporated here by reference.

The ear tips of FIGS. 2A and 3A are made of a soft silicone material with a hardness of less than around 20 A durometer, and in particular of around OO50 durometer or less. As described above, such soft material is generally tacky and has a high coefficient of friction, greater than 3 (unitless) measured per ASTM standard D1894. To decrease the tackiness and friction and thereby achieve a better fit, a coating is applied to the surface to lower the coefficient of friction to less than 2.0, and preferably to as low as 0.2 to 1.0. Although a lubricant could be used, permanent coatings that become part of the ear tip and maintain the desired coefficient of friction without transferring to the wearer are preferred.

In some examples, the coating is a silicone formulation having a lower coefficient of friction than the material used to form the remainder of the ear tip. By using an appropriate silicone, this coating can be bonded to the substrate permanently. One silicone coating found to be effective is MED 6670 from NuSil Silicone Technologies in Santa Barbara, Calif., which may be applied to the ear tip body as a spray-on coating. NuSil's MED 6670 forms an assortment of bumps on the silicone body. Another silicone coating that has been found to be effective is the 1-2620 Dispersion from Dow Corning in Midland, Mich., which forms a uniform layer on the underlying silicone body. Both morphologies advantageously allow the overall ear tip to remain soft and pliable. While a silicone having a lower coefficient of friction may be harder than the soft material of the body, limiting the coating thickness or applying it in discrete bumps allows the coated parts to maintain their shape and overall mechanical properties.

Figure 4:
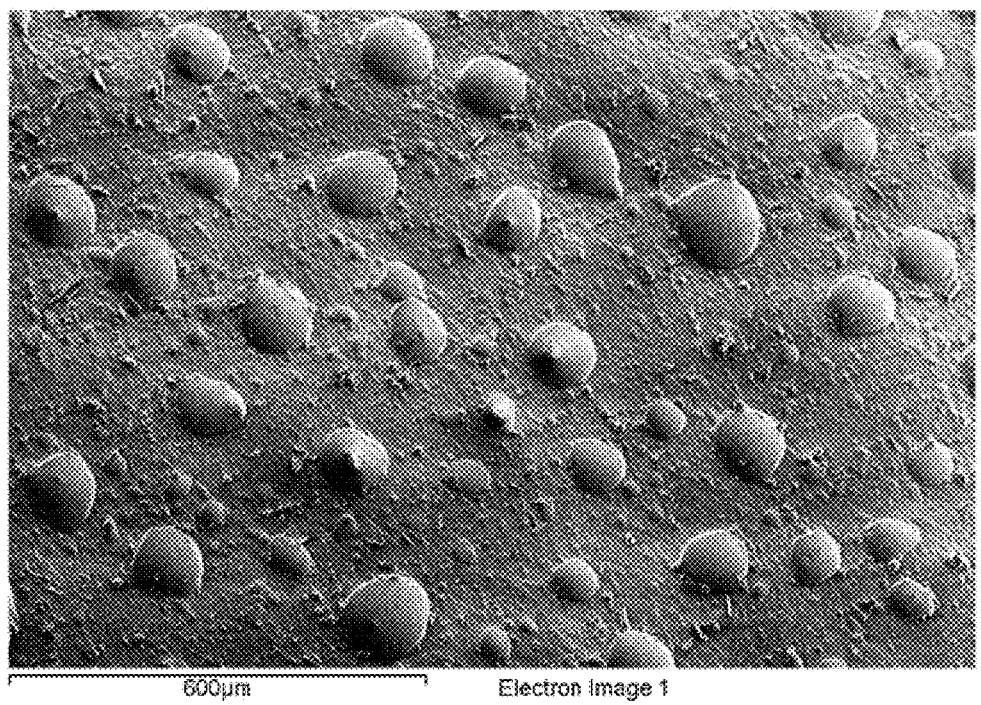
FIGS. 4 and 5 show electron micrographs of ear tip surfaces.

In one example, the ear tip is made almost entirely of silicone of OO40 durometer. The ear tip is further coated with NuSil MED 6670 by spray coating and then curing to result in a bumpy pattern as shown in FIG. 4. This coating creates nodules of around 25-100 μm diameter and around 20 μm high, randomly distributed and spaced around 100 μm apart, with the underlying soft silicone exposed between the nodules. With this coating, the frictional coefficient decreases from >3 (too tacky to be measureable) to 0.2 to 1.0. The benefit of the coating was evaluated in blind tests that compared comfort of ear plugs with and without the coating. More than 80% of test subjects preferred the coated plug.

Figure 5:
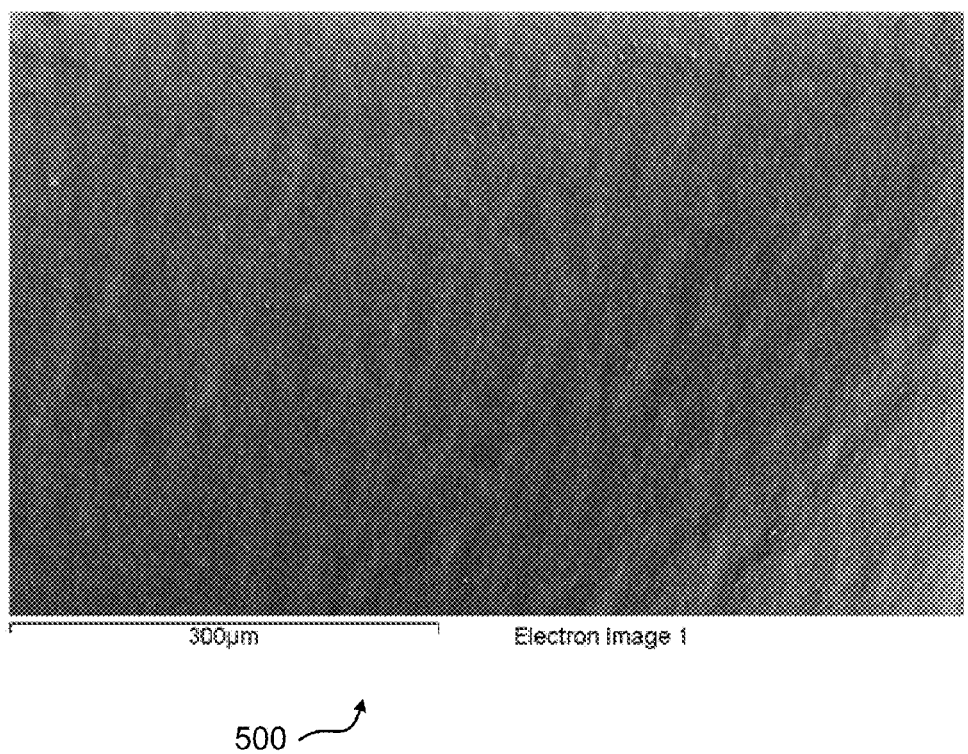

In another example, a part is again made of silicone of 10 A durometer. The part is further coated with Dow 1-2620 by dip coating and then curing to result in a generally uniform coating as shown in FIG. 5. With this coating, the frictional coefficient decreases from between 3 and 4 to between 0.2 and 1.0. Blind tests comparing the uniform coating to the bumpy coating of FIG. 4 revealed that test subjects ranked ear tips having the two different coating morphologies equally, when the ear tip body was made of OO40A silicone but with two above two coating morphologies. Although the Dow 1-2620 has a hardness of 25 D durometer, the coating thickness is thin enough that this relatively greater hardness does not appreciably affect the total hardness of the much softer silicone body. Other silicone coatings, such as Dow 1-2557 and Dow 3715 are also effective.

Coatings made from silicone may be more effective and longer lasting than some alternative treatments, such as lubrication created by silicone oil, that may be useful in other applications. Because both the body of the ear tip and the surface coating are silicone, even though they have different hardness values, they are permanently adhered to each other—the protrusions or coating layer do not come off under normal cleaning processes, for example.

Materials other than silicone may also be used as a surface treatment for the ear tip. For example, vapor deposition is used to apply Parylene (CVD deposited poly(p-xylylene) polymer) which polymerizes on the surface to form a uniform layer. Parylene is normally used as a moisture barrier, but like the NuSil MED 6670 and Dow 1-2620 coatings described above, the Parylene coating decreases the coefficient of friction without significantly changing the other material properties of the ear tip, and without rubbing off on the wearer.

In some examples, only a portion of the ear tip is coated by masking portions of the ear tip where the surface treatment is not to be applied. For example, the extension 204 or headphone interface 208 of the ear interface 200 of FIGS. 3A and 3B may be left uncoated.

Other implementations are within the scope of the following claims and other claims to which the applicant may be entitled.

What is claimed is:

1. An ear tip comprising:
    a body shaped to fit at least partially into the outer ear of a wearer and comprising a material having a coefficient of friction of greater than 2.0,
    the body having an outer surface having a permanent coating on at least the part shaped to fit into the outer ear with a coefficient of friction of less than 1.0,
    wherein the coating comprises a distinct layer of material having different material properties than the body,
    the layer of material comprising silicone having a coefficient of friction in the range of 0.2 to 1.0.

2. The ear tip of claim 1 wherein the body comprises silicone.

3. The ear tip of claim 1 wherein the material composing the body has a coefficient of friction of greater than 3.0.

4. The ear tip of claim 1 wherein the layer is comprised of a plurality of nodules of the material.

5. The ear tip of claim 4 wherein the nodules each have a diameter between around 25 to 100 µm and a height of around 10 µm, and are spaced around 100 µm apart.

6. The ear tip of claim 1 wherein the coating comprises a layer of NuSil MED 6670 silicone.

7. The ear tip of claim 1 wherein the coating comprises a layer of silicone selected from the group consisting of Dow 1-2620, Dow 1-2557, and Dow 3715.

8. The ear tip of claim 1 wherein the coating comprises Parylene.

9. The ear tip of claim 1 wherein the layer of material has a hardness greater than that of the body.

10. The ear tip of claim 1 wherein the layer of material is uniformly distributed over the body.

11. The ear tip of claim 1 wherein the body has a hardness of 20 A durometer or less.

12. The ear tip of claim 11 wherein the body has a hardness of OO40 durometer.

13. An ear tip comprising:
    a body shaped to fit at least partially into the outer ear of a wearer and comprising a material having a coefficient of friction of greater than 2.0,
    the body having an outer surface having a permanent coating on at least the part shaped to fit into the outer ear with a coefficient of friction of 0.2.

14. The ear tip of claim 13 wherein:
    the coating comprises a distinct layer of material having different material properties than the body.

15. The ear tip of claim 13 wherein the ear tip is shaped to serve as an ear interface for an audio reproduction device.

16. The ear tip of claim 15 wherein the ear tip comprises:
    a cushion section shaped to fit the lower concha of the wearer's ear and having an engagement section for coupling to the audio reproduction device;
    a nozzle shaped to fit at least partially into the ear canal of the wearer's ear; and
    a passage through the ear tip to allow sound generated by the audio reproduction device to pass through the nozzle and into the ear canal.

17. The ear tip of claim 16 further comprising a retention feature extending from the cushion section and shaped to fit along the antihelix of the wearer's ear.

18. The ear tip of claim 13 wherein the coating covers the outer surface over only a portion of the total surface area of the ear tip.

19. A method of fabricating an ear tip, the method comprising:
    filling mold cavity with a material having a coefficient of friction, when cured, of greater than 2.0 to form a body of the ear tip;
    removing the body from the mold; and
    coating the body with a material having a coefficient of friction, when cured, of 0.2.

20. The method of claim 19 wherein coating the body comprises spraying NuSil MED 6670 silicone onto the body.

21. The method of claim 19 wherein coating the body comprises dipping the body into a silicone selected from the group consisting of Dow 1-2620, Dow 1-2557, and Dow 3715.

22. The method of claim 19 wherein coating the body comprises applying Parylene to the body using vapor deposition.

23. A set of headphones for audio reproduction, the set of headphones comprising:
    a pair of earphones, each earphone comprising an electroacoustic transducer inside a housing; and
    a pair of ear interfaces having bodies formed at least in part of silicone having a coefficient of friction of greater than 2.0;
    the ear interfaces each comprising:
        a cushion section shaped to fit the lower concha of the wearer's ear and having an engagement section for coupling to one of the earphones;
        a nozzle shaped to fit at least partially into the ear canal of the wearer's ear;
        a passage through the ear interface, to allow sound generated by the earphone to pass through the nozzle and into the ear canal; and
        an outer surface having a permanent coating with a coefficient of friction of 0.2.

24. The set of headphones of claim 23, further comprising a second pair of ear interfaces formed of the same materials and comprising the same features of the first pair, but wherein the cushion is of a different size.

25. The set of headphones of claim 23 wherein the coating comprises NuSil MED 6670 silicone.

26. The set of headphones of claim 3 wherein the coating comprises a silicone selected from the group consisting of Dow 1-2620, Dow 1-2557, and Dow 3715.

27. The set of headphones of claim 23 wherein the coating comprises Parylene.

28. An ear interface for an audio reproduction device comprising:
    a body shaped to fit at least partially into the outer ear of a wearer and comprising a cushion section shaped to fit the lower concha of the wearer's ear and having an engagement section for coupling to the audio reproduction device;
a nozzle shaped to fit at least partially into the ear canal of the wearer's ear; and
a passage through the ear tip to allow sound generated by the audio reproduction device to pass through the nozzle and into the ear canal; and
a retention feature extending from the cushion section of the body and shaped to fit along the antihelix of the wearer's ear;
the ear interface comprising a material having a coefficient of friction of greater than 2.0, and
the body having an outer surface having a permanent coating on at least the nozzle with a coefficient of friction of 0.2.

* * * * *